(12) United States Patent
McKenzie et al.

(10) Patent No.: US 7,967,772 B2
(45) Date of Patent: Jun. 28, 2011

(54) INJECTOR FOR VISCOUS MATERIALS

(75) Inventors: John R. McKenzie, San Carlos, CA (US); Stanley R. Conston, San Carlos, CA (US); David J. Kupiecki, San Francisco, CA (US)

(73) Assignee: iScience Interventional Corporation, Menlo Park, CA (US)

( * ) Notice: Subject to any disclaimer, the term of this patent is extended or adjusted under 35 U.S.C. 154(b) by 1198 days.

(21) Appl. No.: 10/585,909

(22) PCT Filed: Jan. 12, 2005

(86) PCT No.: PCT/US2005/001123
§ 371 (c)(1),
(2), (4) Date: Jul. 12, 2006

(87) PCT Pub. No.: WO2005/069831
PCT Pub. Date: Aug. 4, 2005

(65) Prior Publication Data
US 2007/0287958 A1    Dec. 13, 2007

Related U.S. Application Data

(60) Provisional application No. 60/536,080, filed on Jan. 12, 2004.

(51) Int. Cl.
*A61N 1/30* (2006.01)
(52) U.S. Cl. .............................................. 604/19
(58) Field of Classification Search .............. 604/890.1, 604/65–67, 131, 19, 232, 240, 239, 234, 604/200–206
See application file for complete search history.

(56) References Cited

U.S. PATENT DOCUMENTS

| | | | |
|---|---|---|---|
| 3,537,453 A | 11/1970 | Drummond et al. | |
| 3,791,560 A | 2/1974 | Harris, Sr. | |
| 3,915,651 A * | 10/1975 | Nishi | 73/864.16 |
| 3,921,864 A | 11/1975 | Dawes | |
| 3,923,207 A | 12/1975 | Kyogoku | |
| 4,004,718 A | 1/1977 | Wesley | |
| 4,384,581 A | 5/1983 | Conway | |
| 4,416,291 A | 11/1983 | Kaufman | |
| 4,439,185 A * | 3/1984 | Lundquist | 604/97.02 |
| 4,529,401 A * | 7/1985 | Leslie et al. | 604/131 |
| 4,641,766 A | 2/1987 | Vlasich | |
| 4,710,178 A * | 12/1987 | Henri et al. | 604/209 |

(Continued)

FOREIGN PATENT DOCUMENTS

AU    75153/87    8/1991

(Continued)

OTHER PUBLICATIONS

International Search Report and Written Opinion dated Oct. 20, 2008, for related Singapore Application No. SG 200604618-9.

(Continued)

*Primary Examiner* — Manuel A Mendez
(74) *Attorney, Agent, or Firm* — Weaver Austin Villeneuve & Sampson LLP

(57) ABSTRACT

An injector is provided to deliver microquantities of viscous materials into the body, such as the eye, for surgical purposes. The injector comprises a syringe body with a plunger disposed therein coupled to a positive displacement mechanism capable of progressively advancing the plunger to precisely deliver microquantities of materials at a constant or predetermined delivery rate.

25 Claims, 5 Drawing Sheets

U.S. PATENT DOCUMENTS

| | | | |
|---|---|---|---|
| 4,883,472 A | | 11/1989 | Michel |
| 4,941,308 A | * | 7/1990 | Grabenkort et al. ............ 53/425 |
| 4,952,205 A | | 8/1990 | Mauerer et al. |
| 5,015,233 A | * | 5/1991 | McGough et al. ......... 604/97.03 |
| 5,019,048 A | | 5/1991 | Margolin |
| 5,135,488 A | * | 8/1992 | Foote et al. ................ 604/97.03 |
| 5,409,457 A | | 4/1995 | del Cerro et al. |
| 5,545,144 A | | 8/1996 | Fryklund et al. |
| 5,647,853 A | | 7/1997 | Feldmann et al. |
| 5,741,554 A | | 4/1998 | Tisone |
| 5,743,960 A | | 4/1998 | Tisone |
| 5,916,524 A | | 6/1999 | Tisone |
| 6,063,057 A | * | 5/2000 | Choh ......................... 604/99.01 |
| 6,102,895 A | | 8/2000 | Cortella et al. |
| 6,352,522 B1 | | 3/2002 | Kim et al. |
| 6,371,963 B1 | | 4/2002 | Nishtala et al. |
| 6,520,928 B1 | | 2/2003 | Junior |
| 6,684,720 B2 | | 2/2004 | Sgourakes |
| 6,766,817 B2 | | 7/2004 | da Silva |
| 6,907,879 B2 | | 6/2005 | Drinan et al. |
| 6,959,615 B2 | | 11/2005 | Gamble |
| 7,112,187 B2 | | 9/2006 | Karlsson |
| 7,207,980 B2 | | 4/2007 | Christian et al. |
| 7,285,255 B2 | | 10/2007 | Kaldec et al. |
| 2003/0055386 A1 | | 3/2003 | Strauss et al. |
| 2004/0069076 A1 | | 4/2004 | Gamble |
| 2004/0231437 A1 | | 11/2004 | Schwartz et al. |
| 2006/0173418 A1 | | 8/2006 | Rinaudo et al. |
| 2006/0292304 A1 | | 12/2006 | Tisone |
| 2007/0118093 A1 | | 5/2007 | von Muhlen et al. |
| 2007/0287958 A1 | | 12/2007 | McKenzie et al. |

FOREIGN PATENT DOCUMENTS

| | | |
|---|---|---|
| ES | 2 055 648 | 8/1994 |
| JP | U56-109741 | 1/1980 |
| WO | WO 96/14893 | 5/1996 |
| WO | WO 03/017854 | 3/2003 |
| WO | WO03/045290 | 6/2003 |
| WO | WO2004/093761 | 11/2004 |

OTHER PUBLICATIONS

Int'l Application No. PCT/US05/01123, Search Report dated Sep. 7, 2006.

Int'l Application No. PCT/US05/01123, Written Opinion dated Sep. 7, 2006.

International Search Report and Written Opinion dated Jan. 29, 2009, for related Singapore Application No. SG 200604618-9.

Search Report and Written Opinion dated May 18, 2009 for International Application No. PCT/US2009/038556.

International Search Report and Written Opinion dated Sep. 5, 2007, for related Singapore Application No. SG 200604618-9.

Examination Report dated Apr. 7, 2010 for Indian Patent Application No. 1962/KOLNP/2006.

Translation of JPU56-109741.

Translation of Office Action dated Aug. 12, 2010 for Japanese Patent Application No. 2006-549602. No. 2006-549602.

Final Office Action dated Sep. 15, 2010 for U.S. Appl. No. 12/412,586.

$2^{nd}$ Examination Report dated Nov. 10, 2010 for Australian Patent Application No. 2005206872.

E-mail dated Jul. 29, 2010 from Elson da Silva re "Respecting Hydrology Science in the Patenting System", regarding U.S. Pat. Application 2010019117.

Office Action dated Jul. 24, 2009 for Chinese Patent Application No. 200580007292.0.

Office Action dated Sep. 9, 2009 for U.S. Appl. No. 12/412,586.

Examination Report dated Oct. 13, 2009 for Australian Patent Application No. 2005206872.

Second Action dated Feb. 5, 2010 for Chinese Patent Application No. 200580007292.0.

Final Office Action dated Mar. 15, 2010 for U.S. Appl. No. 12/412,586.

\* cited by examiner

INJECTOR FOR VISCOUS MATERIALS

RELATED APPLICATIONS

This application is related to International Application No. PCT/US2005/001123 filed on Jan. 12, 2005, the priority of which is claimed pursuant to 35 USC 120 and 363. The priority of provisional U.S. application Ser. No. 60/536,080, filed Jan. 12, 2004, is claimed pursuant to 35 USC 119(e) and 363. The disclosure of both of these applications are incorporated by reference herein in their entirety.

BACKGROUND OF INVENTION

In ophthalmic surgery, a high viscosity material often called a surgical viscoelastic is injected into the eye as a surgical aid. Viscoelastic materials used in ophthalmic surgery include compositions containing hyaluronic acid, chondroitin sulfate or chemically modified cellulose. Due to the unusual shear thinning or thixotropic properties of such materials, viscoelastics are injectable through a small bore needle or cannula, then recoil to a material providing stiff gel-like properties after injection. A viscoelastic is often injected into the anterior chamber of the eye during cataract surgery to maintain the intraocular space and protect the corneal endothelium from mechanical damage. The injection of viscoelastic is used to dilate tissue spaces such as Schlemm's canal during glaucoma surgery. Injection of viscoelastic is also used to dissect tissues such as the lens capsule or retinal membranes.

Viscoelastics are typically delivered to tissues with a syringe under manual control by the surgeon. A hand operated syringe is used to inject the viscoelastic through a needle or cannula attached onto a distal luer connector of the syringe. Due to the high viscosity of the material, it is often difficult to manually produce sufficient force with a syringe, especially with small bore cannulas or needles. In addition, the dynamic flow nature of viscoelastic materials makes it difficult to deliver small amounts in a precise, controlled manner.

The present invention is related to a means for improved delivery of high viscosity materials through a cannula or needle into tissues.

SUMMARY OF THE INVENTION

The present invention provides an injector for viscous materials comprising a syringe body having distal and proximal ends and a hollow bore connecting these ends, the distal end having a fluid outlet. A plunger is disposed within the hollow bore and is coupled to a positive displacement mechanism capable of progressively advancing the plunger toward the distal end to eject fluid material contained within the hollow bore through the fluid outlet.

The positive displacement mechanism may comprise a threaded rod attached to the plunger or a linear translation device having a series of mechanical stops.

The positive displacement mechanism may be coupled to a powered source of motion to provide an even and constant force to drive the plunger.

DESCRIPTION OF INVENTION

The injector of the present invention comprises a syringe body with a proximal end and an opposing distal end, with a hollow bore between the two ends. A plunger is disposed within the hollow bore and is coupled to a mechanism that provides positive displacement of the plunger upon actuation. The positive displacement mechanism allows high precision in delivery of viscous and in particular, viscoelastic materials from the syringe body from the distal end. By "positive displacement" it is meant that force is applied to the plunger and/or the linear translation of the plunger is incrementally restricted in such a way as to provide a constant or incrementally precise, controllable delivery of the materials from the distal end of the syringe body. The positive displacement mechanism may be configured to allow progressive linear translation of the plunger in discrete increments to control delivery. The syringe body has a fluid outlet at the distal end that may terminate in a connector such as a luer fitting for attachment of a needle or cannula.

Figure 1:
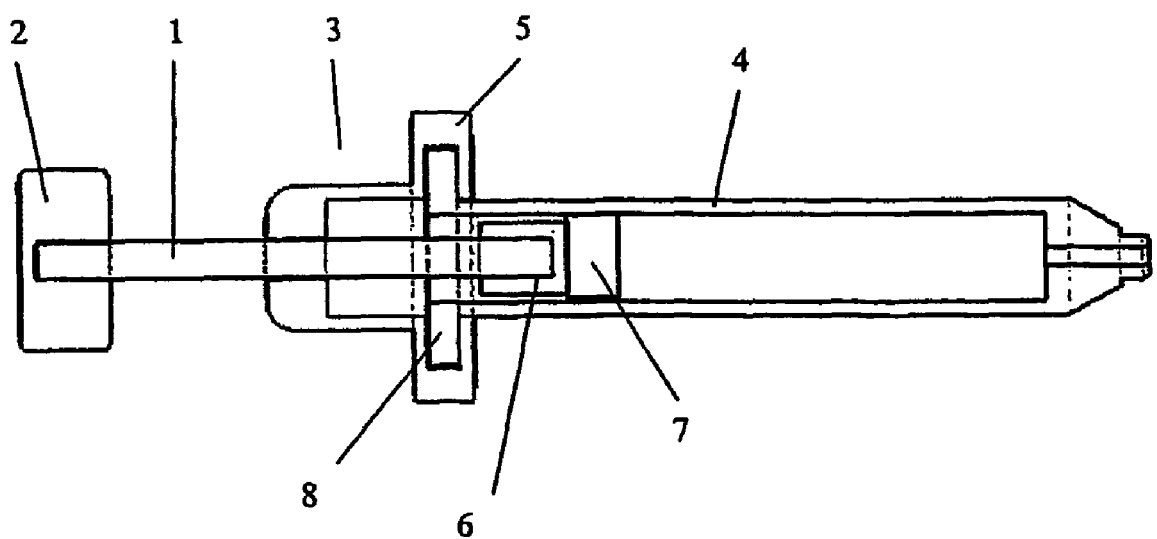
FIG. 1 is a schematic cross-sectional view of a first embodiment of an injector according to the invention.

Referring to FIG. 1, in one embodiment of the injector 3, a threaded rod 1 is attached at its distal end to a plunger 6. The plunger 6 is located within a syringe body 4 having a proximal flange 8. A cap 5 is connected to the flange 8. At the proximal end of the rod 1 is a handle 2 which can serve as a thumbwheel to turn the rod to advance the plunger 6. A stopper 7 is located within the syringe body 4 to form an air tight seal when force of the advancing plunger is applied against the viscous material within the syringe body. The viscous material is ejected through the distal end of the syringe body into an appropriate receiving device.

Figure 2:
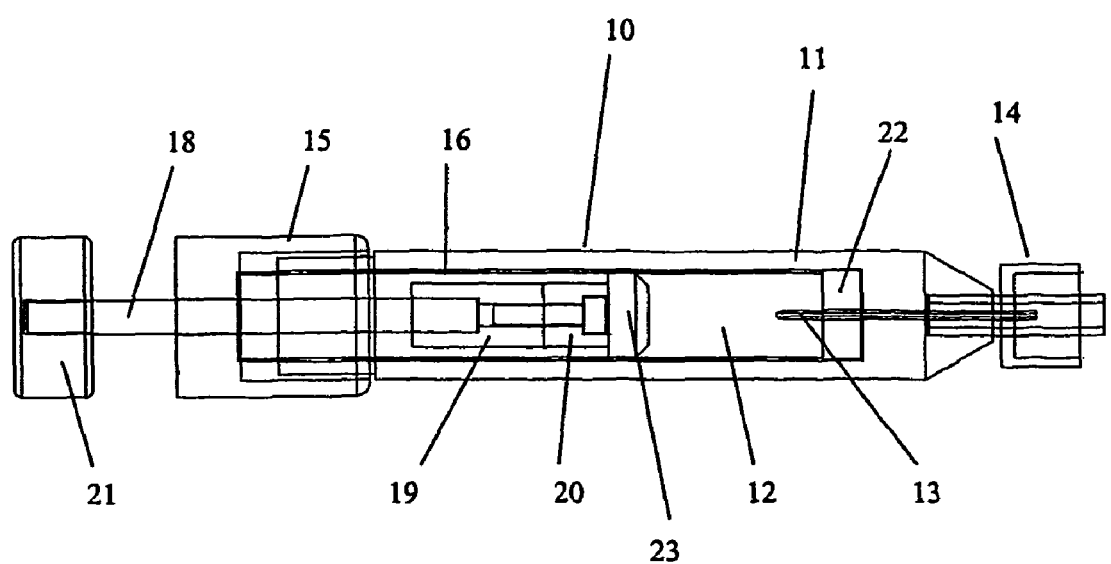
FIG. 2 is a schematic cross-sectional view of a second embodiment of an injector according to the invention.

In another embodiment of an injector 10, referring to FIG. 2, a cartridge 12 prefilled with viscoelastic material and comprising a rubber septum 22 at the distal end can be loaded into the syringe body 11 and then injected in a controlled manner using a screw mechanism comprising a threaded rod 18 attached to a distal plunger assembly 16 comprising a plunger 19, thrust bushing 20 and rubber stopper 23 that move slidably within the syringe body 11. The injector 10 comprises a cap assembly 15 and the syringe body 11. The plunger 19 may have a seal such as an O ring or rubber flange (not shown) to assist in forming a fluid tight seal between the plunger 19 and the syringe body 11. The threaded rod 18 extends out through a mating threaded orifice in the cap assembly 15 at the proximal end of the syringe body 11. Turning the end of the rod 18 advances the plunger 19 to eject the viscous material loaded within a cartridge 12. The cap 15 may be removed to insert the prefilled cartridge 12 into the bore of the syringe body 11. The syringe body incorporates an internal needle 13, at the distal end of the injector to penetrate into the cartridge. The needle provides a flow path from the cartridge to a male luer fitting 14 on the distal end of the injector. The rubber septum 22 provides fluid tight sealing of the cartridge to the internal needle. The internal thrust bushing 20 and rubber stopper 23 at the end of the plunger assembly 16 interface to the proximal end of the cartridge 12. When the injector handle 21 is turned, the threaded rod 18 acts upon the plunger assembly 16 to provide a positive displacement action to the cartridge to deliver the cartridge contents through the distal luer fitting 14.

The use of a positive displacement mechanism insures the precise and repeatable delivery characteristics due to the lack of a compressible component. Injectors according to the invention precisely deliver small increments (microquantities) of a viscous fluid, typically in the range of 5 to 25 microliters. The invention is advantageous particularly because the delivery of small amounts of viscous fluids is difficult when attempting to deliver through a small bore needle, microcannula or microcatheter. The precise delivery of small amounts of a viscous fluid is especially critical in microsurgery where the fluid is used to dilate or dissect delicate tissue structures.

Figure 3:
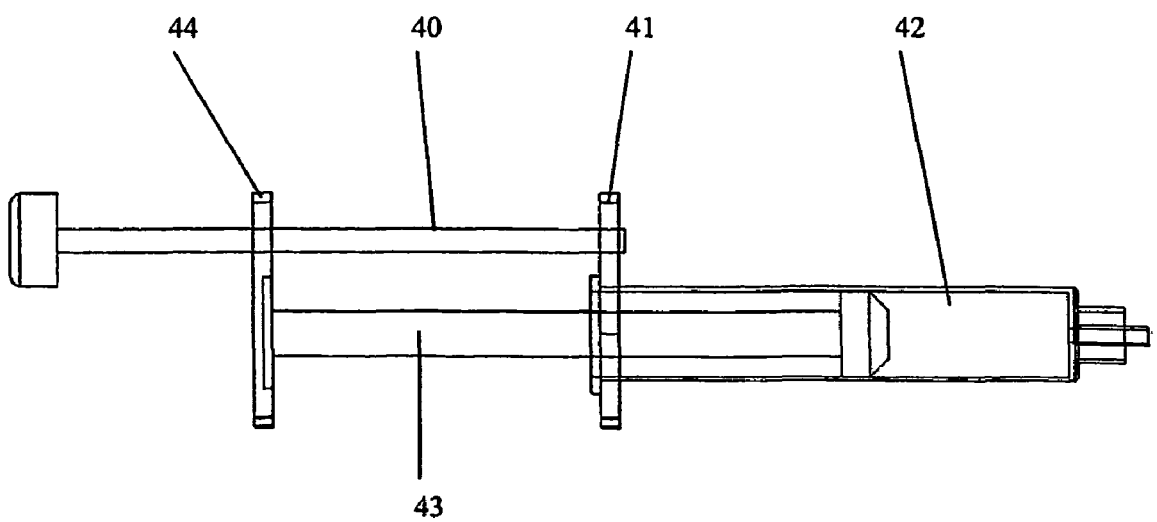
FIG. 3 is a schematic cross-sectional view of a third embodiment of an injector according to the invention.

Referring to FIG. 3, in another embodiment, the positive displacement mechanism comprises a threaded rod 40 that attaches syringe body plate 41 to a plunger plate 44 parallel thereto. Turning of the rod 40 moves the plates 41 and 44 toward or away from each other. Attachment of the plate 41 to the syringe body 42 of the plate 44 to the plunger shaft 43, the plunger is moved to allow precision control of the delivery of material from the syringe body.

In another embodiment, the positive displacement mechanism comprises a plunger with a series of spaced mechanical stops having predetermined spacing arranged to allow linear advancement of the plunger from one mechanical stop to the next. A release mechanism or additional advancement force may be utilized to continue to advance the plunger to the next stop. The amount of plunger translation allowed by each stop may be tailored to set the precision of injector delivery.

In another embodiment, the positive displacement mechanism is attached to a conventional syringe body, allowing it to be used with a variety of prepackaged viscoelastic syringe kits. For example, the mechanism may be attached to the syringe flange and act on or replace the provided plunger.

It is thus also a feature that the injector may be provided in kits including an injector, one or more microcannulae for delivery of materials from the injector to a surgical site, and/or prepackaged cartridges containing viscoelastic material useful in surgical or medical applications The injector may be fabricated from any suitable high strength material such as metals and polymers. Preferred are materials with may be sterilized by conventional means such as by autoclaving, ethylene oxide gas treatment or exposure to ionizing radiation. Suitable materials include metals such as steel and titanium, polymers such as polysulfone, polyethylene, nylon, polymethylmethacrylate, polyethylene terephthalate, polypropylene and polycarbonate.

Figure 4:
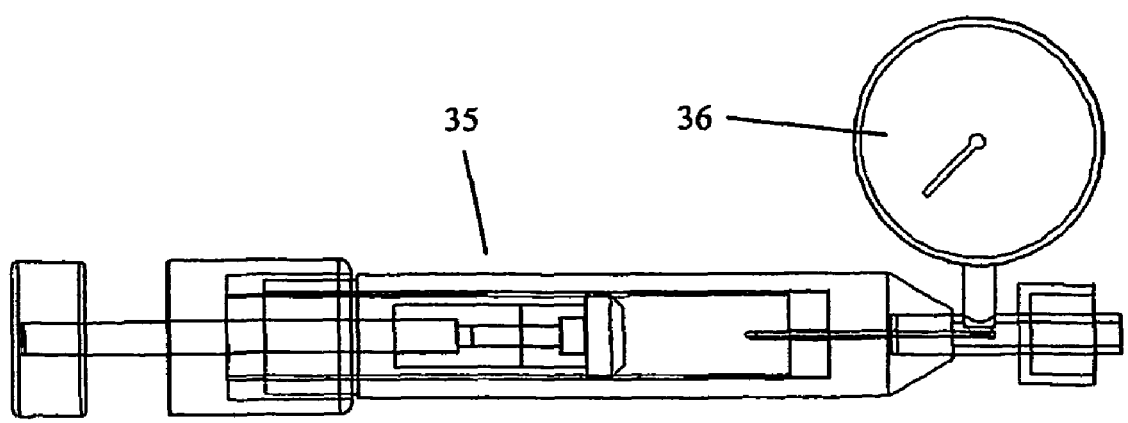
FIG. 4 is a schematic cross-sectional view of a fourth embodiment of an injector according to the invention that accommodates a pressure gauge to measure and regulate pressure at the injector outlet.

The injector may also be used for rate-controlled delivery to precisely deliver viscous fluids at a slow and predetermined flow rate by maintaining a predetermined varied or constant injection pressure. When injecting through a small bore device such as a microcannula or a microcatheter with controlled injection pressure, a constant or predetermined profiled flow rate of viscous fluid results. Regulation of injection pressure measured at the injector output or within the injector allows control of the flow rate. Referring to FIG. 4, pressure regulation may be accomplished by attaching a pressure gauge 36 or transducer to an injector 35. A constant injection pressure may be maintained by manual control of the positive displacement mechanism while monitoring injection pressure or alternatively by electrical feedback to a powered actuator driving the injection mechanism. In an alternate embodiment, pressure regulation may also be accomplished by mechanical means by limiting applied force by the positive displacement mechanism. For example, a clutch mechanism may be integrated into a screw drive mechanism to limit the maximum force applied to delivery the viscous material.

The injector may also incorporate a pressure relief valve into the injector to prevent over pressurization or pressure spike during viscous fluid delivery. The pressure relief valve may consist of a ball and spring assembly, where the ball is pressed across an orifice by spring force until the injection pressure overcomes the spring force to allow fluid flow and pressure release. The relief valve may be designed to allow user adjustment of the maximum injection pressure.

The following examples are provided for the purpose of illustration and are not intended to limit the scope of the invention in any way.

Example 1

An injector was fabricated from a syringe body machined from polycarbonate, designed to receive a prefilled cartridge of viscoelastic material. At its distal end, a sharpened 22 gauge needle was bonded into a small axial through-hole in the syringe body. Concentric with the needle was a counterbore to accept a male luer fitting. The sharpened proximal end of the needle projected into the bore of the syringe in order to puncture the rubber septum of the cartridge when it was loaded into the syringe body. At its proximal end, the syringe body was externally threaded to mate to a cap and plunger assembly. The cap assembly consisted of an internally threaded (½-13 UNC) machined polycarbonate cap with a small threaded (5-40 UNC) hole through its center in which a threaded stainless steel rod was located. Attached to the distal end of the threaded rod was a polycarbonate plunger that had a low friction acetyl thrust bushing fastened to its face. A knurled thumbwheel was attached to the proximal end of the threaded rod. The cartridge of viscoelastic material as supplied by the manufacturer (Advanced Medical Optics Inc.) was sealed with a rubber septum at the distal end and rubber stopper within the bore. Following loading of the cartridge into the bore of the syringe, thereby puncturing the septum, the cap assembly was screwed onto the syringe with the plunger end of the screw inserted into the cartridge bore. The screw was advanced until the thrust bushing contacted the rubber stopper. Continuing to advance the screw resulted in viscoelastic material being ejected from the syringe body through the needle and luer fitting. The acetyl thrust bushing prevented the rotating screw from applying a torque to the stopper and helped maintain the seal of the stopper in the cartridge bore. Based on the pitch of the thread (40 threads per inch) and the bore of the cartridge (6.72 mm), a precise amount of viscoelastic material could be ejected from the syringe.

Screw: 1 revolution=$\frac{1}{40}$ in=0.025 in=0.635 mm
Cartridge bore area: pi*$(6.72)^2$/4=35.4 mm$^2$
Volume/turn: 0.635*35.4=22.5 mm$^3$ Example 2

An injector was fabricated with a screw driven syringe plunger designed to receive a conventional syringe body. The device consisted of a cap portion which had a slot for insertion of the syringe flange, a feed screw for advancement of the plunger, and a thumbwheel for turning the feed screw. In preparation for use, the screw feed was retracted into its proximal most position. The flange on the syringe was then inserted into the slot in the cap, and the syringe bore was aligned with the axis of the cap. The screw was then advanced into the syringe bore until the plunger contacted the stopper in the syringe. Continuing to advance the screw resulted in viscoelastic material being ejected from the syringe body through the needle and luer fitting.

Example 3

The injector of Example 1 was tested for delivery of three surgical viscoelastic materials, Healon, Healon GV, and Healon 5 (Advanced Medical Optics Inc.) with corresponding viscosities at zero shear of 300,000 mPas, 3,000,000 mPas and 7,000,000 mPas. Each viscoelastic material was delivered at ¼, ½, and 1 turn of the screw mechanism of the injector. The resulting material delivered was placed in a tared weigh boat and weighed on an analytical balance (Mettler AG285). The results are shown below in Table 1. The resulting delivery of viscoelastic material from the injector demonstrated linear delivery characteristics in response to the turning of the screw mechanism. Since the viscoelastic materials all had a density close to 1 mg/mm$^3$, the weight of material delivered also demonstrated good correspondence to the calculated volumetric delivery.

TABLE 1

| Injectate | ¼ Turn | ½ Turn | 1 Turn | |
|---|---|---|---|---|
| Healon | 5.11 | 10.74 | 22.53 | milligram |
| Healon GV | 5.63 | 10.87 | 20.60 | milligram |
| Healon 5 | 5.82 | 11.32 | 23.03 | milligram |
| Average | 5.52 | 10.97 | 22.05 | milligram |
| Calculated Volumetric Delivery | 5.625 | 11.25 | 22.5 | mm$^3$ |
| Avg Std Error of Delivery for All Three Injectates | 13.5% | 5.9% | 5.5% | |

Example 4

To demonstrate constant flow delivery of surgical viscoelastic material through an ophthalmic microcannula with a 90 micron diameter lumen (iScience Surgical Corporation, Redwood City, Calif.), the injector of Example 1 was attached to the microcannula in series with a pressure gauge. The viscoelastic material (Healon GV, Advanced Medical Optics Inc.) was delivered to fill the system. The injector screw was tightened to achieve a delivery pressure of 300 psi, +−5%, and held in that range for 60 seconds. All of the fluid expressed from the tip of the microcannula during that period was captured in a dish and weighed. The data from five tests was then averaged and the standard deviation calculated. The results are shown in Table 2.

TABLE 2

| Test Number | Mass of Expressed Viscoelastic (grams) |
|---|---|
| 1 | 0.0048 |
| 2 | 0.0060 |
| 3 | 0.0056 |
| 4 | 0.0049 |
| 5 | 0.0055 |
| Average | 0.00536 |
| Std Dev | 0.00050 |

The injector delivered a constant flow of viscoelastic material of approximately 5.4 milligrams per minute, corresponding to approximately 5.4 microliters per minute.

Example 5

Figure 5:
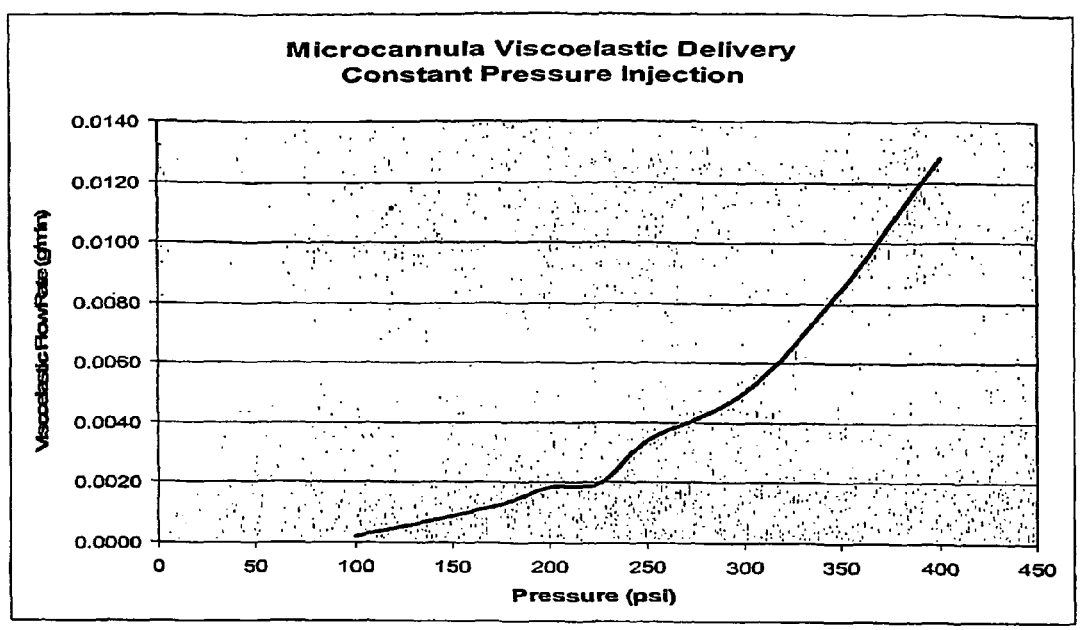
FIG. 5 is a graph of pressure v. flow rate of delivery of viscoelastic material from an injector as described in Example 5.

To demonstrate the ability to control constant flow delivery, the rate of fluid flow of surgical viscoelastic material (Healon GV, Advanced Medical Optics, Inc.) through an ophthalmic microcannula with a 90 micron diameter lumen (iScience Surgical Corporation) at a series of fixed pressures between 100 and 400 psi was measured. A minimum of three samples were tested three times at each pressure, and a total of nine pressure levels were tested (100, 150, 175, 200, 225, 250, 300, 350, and 400 psi). Each sample was tested by connecting the positive displacement injector of Example 1 in series with a calibrated pressure gauge and then to the microcannnula. The screw feed on the injector was advanced until viscoelastic material filled the microcannula and was expressed from the distal tip. The rate of screw advancement was then manually adjusted to keep the infusion pressure at the target level. The target pressure level was maintained for a minimum of three minutes and viscoelastic fluid was captured in a small cup. At the conclusion of the three minutes the expressed viscoelastic fluid was weighed and the flow rate calculated. Referring to FIG. 5, the data on the graph represents the average values at each pressure.

The invention claimed is:

1. A device for delivering microquantities of viscous materials comprising
    an injector for delivery of viscous materials from a cartridge containing a prepackaged quantity of said viscous materials, said injector comprising a syringe body with a proximal end, a distal end with an outlet and a hollow bore between the ends sized and shaped to receive said cartridge;
    an internal needle in communication with said outlet and internal to the distal end of said injector, said internal needle located for penetration of said cartridge;
    and a plunger disposed within the hollow bore coupled to a positive displacement mechanism that progressively advances the plunger toward the distal end of the syringe body to eject the material within a cartridge in the hollow bore through said outlet; and
    a microcannula or microcatheter attached to said outlet in communication with said needle.

2. A device according to claim 1 wherein said microquantities are in the range of about 5 to 25 microliters.

3. The device according to claim 1 wherein in said injector said positive displacement mechanism comprises a threaded rod attached to said plunger.

4. The device according to claim 3 wherein said threaded rod has a thread pitch greater than or equal to 40 threads per inch.

5. The device according to claim 1 wherein in said injector said positive displacement mechanism comprises a linear translation mechanism with a series of spaced mechanical stops.

6. The device according to claim 1 wherein in said injector said positive displacement mechanism is coupled to a powered source of motion.

7. The device according to claim 1 wherein in said injector said positive displacement mechanism provides a repeatable increment of delivered volume of material of less than about 25 microliters.

8. The device according to claim 1 wherein said injector additionally comprising means for regulation of the injection pressure.

9. The device according to claim 8 wherein said means for regulation of the injection pressure comprises an attenuator to limit the force applied to eject said material.

10. The device according to claim 9 wherein said attenuator comprises a clutch engageable to said positive displacement mechanism.

11. The device according to claim 1 wherein said injector additionally comprising an injector pressure monitor.

12. The device according to claim 11 wherein said monitor provides feedback information on pressure to an actuator, wherein said actuator provides power to drive said positive displacement mechanism.

13. The device according to claim 1 wherein said injector additionally comprises a pressure relief valve to relieve pressure within said hollow bore.

14. The device according to claim 1 wherein said injector further comprises an internal needle within said hollow bore for penetration of said cartridge to provide a flow path from within said cartridge to said outlet.

15. A kit for delivering microquantities of viscous materials comprising
- an injector for delivery of viscous materials from a cartridge containing a prepackaged quantity of said viscous materials, said injector comprising a syringe body with a proximal end, a distal end with an outlet and a hollow bore between the ends sized and shaped to receive said cartridge;
- an internal needle in communication with said outlet and internal to the distal end of said injector, said internal needle located for penetration of said cartridge;
- and a plunger disposed within the hollow bore coupled to a positive displacement mechanism that progressively advances the plunger toward the distal end of the syringe body to eject the material within a cartridge in the hollow bore through said outlet; and
- a microcannula or microcatheter adapted for attachment to said outlet in communication with said needle.

16. The kit according to claim 15 wherein said positive displacement mechanism comprises a threaded rod attached to said plunger having a thread pitch greater than or equal to 40 threads per inch.

17. The kit according to claim 15 wherein said positive displacement mechanism comprises a series of spaced mechanical stops for controlling the linear displacement of said plunger.

18. The kit according to claim 15 wherein in said injector said positive displacement mechanism provides a repeatable increment of delivered volume of material of less than about 25 microliters.

19. The kit according to claim 15 wherein in said injector said positive displacement mechanism is coupled to a powered source of motion.

20. The kit according to claim 15 wherein said injector additionally comprises a regulator of the injection pressure, said regulator comprising an attenuator to limit the force applied to eject said material.

21. The kit according to claim 20 wherein said attenuator comprises a clutch engageable to said positive displacement mechanism.

22. The kit according to claim 15 wherein said injector additionally comprises an injector pressure monitor to provide feedback information on pressure to an actuator, wherein said actuator provides power to drive said positive displacement mechanism.

23. The kit according to claim 15 wherein said injector additionally comprises a pressure relief valve to relieve pressure within said hollow bore.

24. The kit according to claim 15 comprising a plurality of microcannulae.

25. The kit according to claim 15 wherein said injector further comprises an internal needle within said hollow bore for penetration of said cartridge to provide a flow path from within said cartridge to said outlet.

* * * * *